United States Patent [19]

Hosang et al.

[11] Patent Number: 5,298,616
[45] Date of Patent: Mar. 29, 1994

[54] SULFATED O-POLYSACCHARIDE-TREHALOSES

[75] Inventors: Markus Hosang, Allschwil; Niggi Iberg, Basle, both of Switzerland; Michel Trumtel, Gien, France; Thomas B. Tschopp, Ettingen, Switzerland; Hans P. Wessel, Heitersheim, Fed. Rep. of Germany

[73] Assignee: Hoffmann-La Roche Inc., Nutley, N.J.

[21] Appl. No.: 764,511

[22] Filed: Sep. 20, 1991

[30] Foreign Application Priority Data

Oct. 3, 1990 [CH] Switzerland ............... 3177/90
Jul. 30, 1991 [CH] Switzerland ............... 2267/91

[51] Int. Cl.$^5$ ............................. C07H 11/00
[52] U.S. Cl. .................... 536/118; 536/121; 536/122; 536/1.11; 536/123.1
[58] Field of Search ................ 536/118, 122, 1.1, 121

[56] References Cited

U.S. PATENT DOCUMENTS

| | | | |
|---|---|---|---|
| 4,021,544 | 5/1977 | Nair et al. | 536/118 |
| 4,098,995 | 7/1978 | Nair et al. | 536/118 |
| 4,221,907 | 9/1980 | Nair et al. | 536/118 |
| 4,357,326 | 11/1982 | Nair et al. | 536/118 |
| 4,359,458 | 11/1982 | Nair et al. | 536/118 |
| 4,885,361 | 12/1989 | Wessel | 536/118 |

FOREIGN PATENT DOCUMENTS

| | | |
|---|---|---|
| 0230023 | 7/1987 | European Pat. Off. . |
| 0301618 | 1/1989 | European Pat. Off. . |
| 1381426 | 1/1975 | United Kingdom . |

OTHER PUBLICATIONS

Goren et al., Biochemistry, 15:2728–2735 (1976).
Liav et al., Chem. Abstracts, 101:692 (1984).
Liav et al., Carbohydrate Research, 127:211–216 (1984).
Wessel et al., Helv. Chim. Acta, 74:682–696 (1991).
Fieser and Fieser, Advanced of Organic Chemistry, pp. 930–933, Reinhold Publishing Corp. 1961.
Streitwieser and Heathcock, Introduction to Organic Chemistry, pp. 612 and 698, 1976 [MacMillan Publishing Co., Inc. New York].
Yokose and Ogawa, et al., Journal of Antibiotics, pp. 1166–1175 [Sep. 1983].

*Primary Examiner*—Johnnie R. Brown
*Assistant Examiner*—Everett White
*Attorney, Agent, or Firm*—George M. Gould; William H. Epstein

[57] ABSTRACT

Sulphated O-Polysaccharide-trehaloses which can be used as medicaments, especially for the treatment of arteriosclerotic disorders.

22 Claims, No Drawings

SULFATED O-POLYSACCHARIDE-TREHALOSES

SUMMARY OF THE INVENTION

In accordance with this invention, we have discovered that novel sulfated oligosaccharies of the formula:

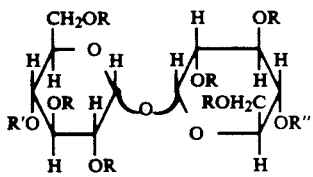

wherein R is hydrogen or the sulfate residue —$SO_3M$; M is a cation; R' is a an equatorially or quasiequatorially linked mono- di- or tri- saccharide; or an axially linked trisaccharide; and R" is hydrogen or an equatorially or quasiequatorially linked mono- or disaccharide with said mono-, di- or tri-saccharides which forms the substituents R' and R" being sulfonated with said sulfate residue; whereby the oligosaccharide contains a maximum of 6 monosaccharide units and an average of at least one —$SO_3M$ residue per monosaccharide unit,
inhibit the migration and proliferation of cells of the vascular smooth musculature and prevent proliferative arteriosclerotic lesions.

DETAILED DESCRIPTION OF THE INVENTION

The oligosaccharides of this invention which are mono- di- or tri-saccharides ether derivatives of trehalose are formed with 3 to 6 monosaccharide ring units. The minimum monosaccharide ring units contained by the compound of formula I will be 3 since trehalose is a disaccharide and R' and R" together contain at least one mono-saccharide ring unit. Therefore, when R' is a monosaccharide and R" is hydrogen, the resulting compound of formula I will contain 3 monosaccharide units. In accordance with this invention, the compound of formula I contains a maximum of 6 monosaccharide units. Each monosaccharide ring unit contains a heterocyclic ring structure with oxygen being the only hetero atom in the ring. Generally, in accordance with this invention it is preferred that the heterocyclic ring contain 5 or 6 members. In addition, each monosaccharide ring contains free hydroxy groups which in accordance with this invention are sulfated to the extent defined herein. In accordance with this invention, the hydrogens from these free hydroxy radicals are replaced with the sulfate residue so that the oligosaccharide has an average of at least one sulfate residue per monosaccharide unit. If desired all or a portion of the hydrogen atoms of the free hydroxy groups in the oligosaccharides of this invention can be substituted with the aforementioned sulfate residue.

In accordance with this invention, R' can be any equatorially or quasiequatorially linked sulfated mono- di- or tri-saccharide residue or axially liked tri-saccharide residue and R" can be any equatorially or quasiequatorially linked mono or disaccharide.

In accordance with this invention, M can be any conventional cation. The cation M includes all physiologically compatible cations, e.g. alkali metal cations such as $Na+$ and $K+$; ammonium ions and substituted ammonium ions which are derived from tertiary amines such as triethylamine, or pyridine or imidazole; or quaternary ammonium ions such as dodecyltrimethylammonium, ethylpyridinium and benzethonium; as well as alkaline earth metal cations such as $Ca++$. Compounds in which M is $Na+$ are preferred.

The degree of sulphation [AS] designates the number of —$SO_3M$ residues per monosaccharide unit which are present in the molecule on average. The degree of sulphation 1 therefore exists e.g. when a hexasaccharide of formula I contains 6 —$SO_3M$ residues in the molecule. The degree of sulphation in the compounds of formula I preferably amounts to 2–3.

Equatorially linked sulphated mono-, di- or trisaccharide residues R' are preferably $\beta$-glycosidically linked residues; but an equatorial linking, e.g. in the case of arabinose glycosides, can accompany an $\alpha$-glycosidically bonding of the residue R' to the trehalose residue. The term "quasiequatorial" relates to the conformation of furanosides.

In accordance with this invention any conventional mono-, dior trisaccharide can be utilized as R' and R". The compounds of formula I can be manufactured in accordance with the invention by treating a corresponding tri-, tetra-, penta- or hexasaccharide with a sulphating agent and isolating the reaction product of formula I. Examples of monosaccharide residues are glucopyranosyl, mannopyranosyl, arabinopyranosyl, galactofuranosyl, arabinofuranosyl, ribofuranosyl and rhamnofuranosyl. Examples of disaccharide residues are maltosyl, cellobiosyl, lactosyl, melibiosyl, gentiobiosyl and galactopyranosidoarabinopyranosyl. A trisaccharide residue is, for example, maltotriosyl. The aforementioned residues are sulphated as substituents R' or R" in the scope of the definition of formula I. Examples of compounds of formula I are the compounds of formulae Ia and Ib in which R has the significance given above and on average a least one residue R per monosaccharide unit is —$SO_3M$. In the compound Ia R' is $\beta$-D-maltotriosyl and R" is hydrogen, in the compound Ib R' and R" are $\beta$-D-maltosyl.

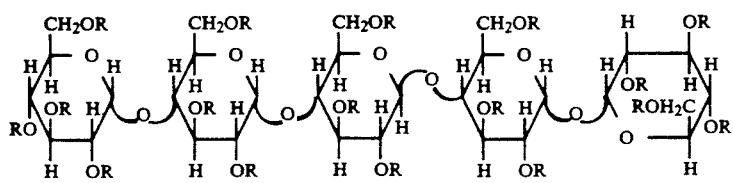

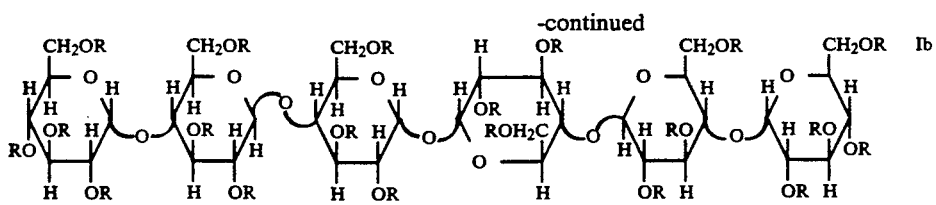

The sulphation in accordance with the present invention can be carried out using methods which are known per se for the sulphation of hydroxy groups. Examples of sulphating agents which can be used for the manufacture of the compounds of formula I are $SO_3$. complexes such as $SO_3$. pyridine, $SO_3$. trimethylamine, $SO_3$. dioxan and $SO_3$. dimethylformamide. Other examples of sulphating agents are chlorosulphonic acid, mixtures of chlorosulphonic acid and sulphuric acid; and piperidine N-sulphate.

The sulfation reaction is conveniently effected in a suitable solvent, especially a polar solvent, e.g. dimethylformamide, dimethyl sulphoxide or hexamethylphosphortriamide. This reaction can be carried out at room temperature or a higher temperature, e.g. at 20°-70° C., whereby the degree of sulphation can be influenced by varying the reaction duration and reaction temperature. The degree of sulphation achieved in each case can be estimated by I-IPLC utilizing conventional methods to determining the degree of sulfation. Furthermore, the degree of sulfation can be assessed by integration of the proper signals in the $^1H$ NMR spectrum of sulfated oligosaccharides with proton containing counterions (e.g. trimethylammonium, pyridinium ion). Another possibility for the assessment of the degree of sulfation is elemental analysis. The working-up of the reaction mixture and, respectively, the isolation of the reaction product of formula I from the reaction mixture, having the desired degree of sulfation can be effected according to methods known per se, e.g. by gel filtration or ultrafiltration. For gel filtration, crosslinked polysaccharide gels such as SEPHADEX LH 20 or G 25 can be used.

The free saccharides which are used as starting materials are known and obtainable by conventional procedures. Enzymatic or synthetic chemical procedures come into consideration for the preparation. The oligosaccharides can be synthesized principally using sequential synthesis or block synthesis. In this case glycosidic bonds are formed by reacting a glycosyl acceptor with a glycosyl donor in the presence of a suitable catalyst. Derivatized glycosyl compounds which are activated at the anomeric centre, such as e.g. chlorides, bromides, fluorides, acetates, trichloroacetimidates, alkylthio derivatives, etc, are suitable as glycosyl donors.

Those saccharide derivatives in which the OH groups to be glycosylated are free and the remaining OH groups are completely or partially protected are suitable as glycosyl acceptors. When the remaining OH groups are only partially protected the glycosydation can be effected selectively or can be directed in a particular direction by virtue of the hydroxyl groups having a different environment.

The compounds of formula I inhibit the migration and proliferation of cells of the vascular smooth musculature and prevent proliferative arteriosclerotic lesions. Their blood coagulation-inhibiting activity is lower than that of heparin. In particular, the compounds have no in vitro anticoagulant activity, i.e. they have no effect or only a very slight effect on the coagulation factors thrombin (F.IIa) and F.Xa. The compounds of formula I can therefore be used for the prophylaxis of arteriosclerotic disorders, in man especially after bypass operations or angioplasty, as well as for the treatment of patients having progressive arteriosclerosis.

The blood coagulation-inhibiting activity was determined as follows:

aPTT (activated partial thromboplastin time) Test (see Walenga et al., CRC Critical Reviews in Laboratory Sciences 22 (4) 361–389 (1986)): 100 μl of citrated human plasma, which contains various concentrations of test compound, is incubated at 37° C. for 8 minutes with 100 μl of Activated Thrombofax (Ortho Diagnostics, Raritan, N.J., U.S.A.). 100 μl of prewarmed 25 mM calcium chloride solution are then added and the coagulation time is measured in a Fibrometer Coagulation Timer (Becton Dickinson, Basle).

anti-Xa Clotting Assay: 25 μl of citrated plasma having various concentrations of test compound are mixed with 75 μl of Factor Xa (Diagnostic Reagents, Thame, Oxon, Great Britain) diluted 1:100 in 0.63% citrate buffer (pH 7.3) which contains 41 mM imidazole, 82 mM NaCl and 0.1% albumin. After warming to 37° C. for 2 minutes 200 μl of a 1:1 mixture of Factor X Deficient Plasma (Diagnostic Reagents) and Platelet Substitute (Diagnostic Reagents) are added and the mixture is incubated at 37° C. for 20 seconds. After the addition of 100 μl of prewarmed 50 mM calcium chloride solution the coagulation time is measured in a Fibrometer.

The activity of the test compound is given as the $IC_{50}$, which is that concentration [μg/ml] which leads to a coagulation time which is double the control value.

Inhibition of Thrombin or Factor Xa in the Chromogenic Substrate Assay (Teien et al., Thrombosis Research 10, 399–410 (1977)): The test was performed in a Cobas-Bio centrifugal automatic spectrophotometer. The buffer solution used consisted of 50 mM Tris buffer, 180 mM NaCl, 7.5 mM EDTA $Na_2$, 1% PEG 6000 and 0.02% Tween 80, pH 8.4. The sample consisted of 50 μl of buffer, 30 μl of anti-thrombin III (1 U/ml), Kabi Diagnostics) and 20 μl of plasma which contained various concentrations of test compounds. 30 μl of sample solution and 20 μl of water with 180 μl of thrombin were added to the test cuvette in the automatic analyzer. After incubation at 37° C. for 240 seconds 60 μl of S-2238 (H-D-Phe-Pip-Arg-NH.pNA, Kabi Diagnostics, Mondal, Sweden, 0.75 mM in water) and 20 μl of water were added. The liberation of pNA (p-nitroaniline) was followed during 60 seconds at 405 nm in 10 second intervals in comparison to water as the blank. The inhibitory activity is given as the $IC_{50}$, which is the concentration [μg/ml] at which the amidolytic activity of thrombin is reduced by 50% in comparison to the plasma control value.

The inhibition of Factor Xa was measured in the same manner using a solution of Factor Xa (2.8 nkat/ml and 2 mM S-2222 (Bz-CO-Ile-Glu-Arg-NH.pNA, Kabi Diagnostics) in water in place of thrombin and, respectively, S-2238.

The anti-proliferative activity of the substances was determined in cell cultures as follows: rat smooth muscle cells (cultivated in DMEM with 10% FCS at 37° C. and 5% $CO_2$) were seeded in 24 well cell culture plates with a density of $8 \times 10^3$ cells/well. After 4 hours the number of adhered cells was determined and the substances to be tested (100 mg/ml) were added. Cells to which no substance was added served as a comparison and heparin (100 µg/ml) served as a positive control. The cells were incubated for 7 days and then the cell number was determined. The antiproliferative activity of the individual substances was calculated as the % inhibition in comparison to non-inhibited growth:

$$\% \text{ Inhibition} = \frac{\text{cell number}_{(-)} - \text{cell number}_{(inhib)}}{\text{cell number}_{(-)} - \text{cell number}_{(d=0)}} \times 100$$

wherein cell number(d=O) cell number after 4 h
cell number(−)=cell number to which no test substances was added, after 7 days.
cell number(inhib)=cell number with 100 µg/ml of the test substance.

The results obtained in the experimental procedures described above with compounds of formula I are listed in Table 1. Heparin served as the reference compound.

TABLE I

| Compound of Example | Anti-proliferative activity % inhibition | Anti-coagulation activity $IC_{50}$ [µg/ml] | | | |
|---|---|---|---|---|---|
| | | Coagulation inhibition aPTT | Xa | Amidolytic activity Thrombin | F.Xa |
| 1G. | 57 | 11 | 31 | >1000 | 960 |
| 2C | 38 | 40 | 115 | >1000 | >1000 |
| 3C | 59 | 12 | 33.5 | >1000 | >1000 |
| 4C | 64 | 11 | 32 | >1000 | >1000 |
| 5C | 39 | 33 | 69 | >1000 | >1000 |
| 6D | 67 | 14.5 | 28.5 | >1000 | 900 |
| 7C | 49 | 13.5 | 34 | >1000 | >1000 |
| Heparin | 47 | 1.2 | 0.6 | 1.9 | 2.7 |

The test results show that the compounds in accordance with the invention have an anti-proliferative activity which, in contrast to the likewise anti-proliferatively active heparin, is not accompanied by or is accompanied to a very insignificant extent by an anticoagulant activity.

The medicaments based on the compounds in accordance with the invention can be administered enterally, e.g orally in the form of tablets, coated tablets, dragées, hard and soft gelatine capsules, solutions, emulsions or suspensions, or rectally, e.g. in the form of suppositories. However, the administration is preferably effected parenterally, e.g. in the form of injection solutions.

For the manufacture of tablets, coated tablets, dragées and hard gelatine capsules the active ingredient can be mixed with pharmaceutically inert, inorganic or organic excipients. As such excipients for tablets, dragdes and hard gelatine capsules there can be used e.g. lactose, maize starch or derivatives thereof, talc, stearic acid or its salts. Suitable excipients for soft gelatine capsules are e.g. vegetable oils, waxes, fats, semi-solid and liquid polyels; depending on the nature of the active ingredient no excipients are, however, usually required in the case of soft gelatine capsules. Suitable excipients for the manufacture of solutions and syrups are e.g. water, polyols, saccharose, invert sugar and glucose, suitable excipients for injection solutions are e.g. water, alcohols, polyols, glycerine and vegetable oils and suitable excipients for suppositories are e.g. natural or hardened oils, waxes, fats and semi-liquid or liquid polyels.

The pharmaceutical preparations can contain, in addition, preservatives, solubilizers, stabilizers, wetting agents, emulsifiers, sweeteners, colorants, flavorants, salts for varying the osmotic pressure, buffers, coating agents or antioxidants. In the case of enteral administration the resorption of the active ingredient can be increased with the aid of liposomes.

The dosage of the active ingredient can vary within wide limits and will, of course, be fitted to the individual requirements in each particular case. In general, in the case of parenteral administration a dosage of about 0.1 to 100 mg/kg, preferably of about 1.5 to 15 mg/kg, per day should be appropriate for adults, although the upper limit just given can also be exceeded when this is shown to be indicated.

EXAMPLE 1

A. A solution of 28.5 g of 2,2',3,3'-tetra-O-benzyl-4,6-O-benzylidene-(α,α-D-trehalose (Carbohydr. Res. 63, 51 (1978)) and 27 ml of bistributyltin oxide in 2.2 l of toluene was heated under reflex for 4.5 hours in a Dean Stark apparatus and reduced to a volume of 800 ml. Subsequently, 3.84 g of tetrabutylammonium bromide and 42.8 ml of benzyl bromide were added and the mixture was stirred at 100° C. After 16 hours the solution was cooled and worked-up by extraction in a sodium hydrogen carbonate/methylene chloride system. The combined organic phases were dried ($MgSO_4$) and chromatographed on silica gel with acetone/hexane 1:2 (containing 1% Of triethylamine) as the eluent. Product fractions were crystailized and gave 27.5 g (86%) of 2,2',3,3',6'-penta-O,-benzyl -4,6-O-benzylidene-α,α-D-trehalose, m.p. 122° C.

B. A solution of 32.7 g of deca-O-acetyl-a-D-maltotriosyl bromide (K. Tabeo, K. Mine and T. Kuge, Carbohydr. Res 48, 197 (1976)), in 85 ml of allyl alcohol was stirred at 50°-60° C. for 90 minutes in the presence of 8.5 g of mercury-11 cyanide, concentrated and extracted in ethereal solution successively with 1 molar potassium iodide solution, sodium bicarbonate solution, and water. Chromatography of the crude product on silica gel with ethyl acetate/hexane 1:1 as the eluent gave 25.3 g (79.6%) of pure allyl deca-O-acetyl-β-D-maltotrioside, $[α]^D_{20} = 75.0°$ (c=0.5, dioxane).

C. A solution of 24.8 g of allyl deca-O-acetyl-β-D-malto- trioside in 150 ml of methanol was stirred at room temperature for 18 hours in the presence of catalytic amounts of anhydrous sodium carbonate, then filtered and neutralized with acidic ion exchanger.

After removing the solvent the residue was taken up in 350 ml of dimethylformamide and treated at room temperature with 8.0 g of sodium hydride (80% in refined oil). After stiffing for 90 minutes the mixture was cooled to 1° C., treated with 32 ml of benzyl bromide and stirred while cooling with ice for 30 minutes and at room temperature for 1 hour. Thereafter, the mixture was added dropwise to 100 ml of methanol and stirred for 1 hour. The reaction mixture was concentrated, taken up in ethyl acetate and extracted with aqueous sodium bicarbonate solution and with water. The organic phases were dried and concentrated (38.5 g). 5 g of benzylated crude product were suspended in 40 ml of acetic acid/water 9:1 and treated in an ultrasonic bath for 3 hours in the presence of 2.46 g of palladium chloride and 2.46 g of sodium acetate. Thereafter, the mixture was suction filtered, washed and evaporated. The residue was taken up in ethyl acetate and the solution was washed in succession with aqueous sodium bicarbonate solution and water. The ethyl acetate phases were dried ($Na_2SO_4$), concentrated and chromatographed on silica gel with toluene/ethyl acetate 7:1 as the eluent. There were obtained 3.99 g (90%) of syrupy deca-O-benzyl-D-maltotriose.

D. A solution of 0.25 ml of oxalyl chloride in 7 ml of absolute dichloromethane was added dropwise at 30° C. during 45 minutes to a solution of 3.69 g of deca-O-benzyl-D-maltotriose in 25 ml of absolute dichloromethane and 0.1 ml of absolute dimethylformamide. After stirring at room temperature for 6 hours the mixture was evaporated. The dried crude deca-O-benzyl-α-D-maltotriosyl chloride was dissolved in 10 ml of absolute acetonitrile and stirred at room temperature for 3 hours in the presence of 0.97 g of dry silver fluoride. The reaction mixture was filtered and the precipitate was washed with ether. The organic solutions were treated with aqueous saturated sodium chloride solution and stirred vigorously for 15 minutes. After suction filtration of the separated precipitate the filtrate was concentrated, diluted with ether and washed in succession with sodium chloride solution and water. The ethereal solutions were evaporated. Chromatography on silica gel with ethyl acetate/ hexane 1:6 as the eluent gave 2.19 g (66%) of pure deca-O-benzyl-β-D-maltotriosyl fluoride, $[\alpha]_D^{20} = 58.9°$ (c=0.9, $CHCl_3$).

E. A solution of 110 ml of trifluoromethanesulphonic anhydride in 5 ml of dry ether was added dropwise at −20° C. within 1 hour in the presence of molecular sieves (4 Å) to a solution of 1.69 g of well dried deca-O-benzyl-β-D-maltotriosyl fluoride and 538 mg of 2,2′,3,3′,6′-penta-O-benzyl-4,6-O-benzylidene-α,α-D-trehalose in 20 ml of dry ether. The mixture was warmed to room temperature and stirred for 48 hours. After filtration over a filter aid, washing with ether and concentrating the residue was chromatographed on silica gel using toluene/ ethyl acetate 14:1 as the eluent. There were obtained 414 mg (30%) of 2,2′,3,3′,6′-penta-O-benzyl-4′-O-(deca-O-benzyl -(α-D-maltotriosyl)-4,6-O-benzylidene-(α,α-D-trehalose as a syrupy product, $[\alpha]_D^{20} = +44°$ (c=0.0846, ETOH)

F. A solution of 295 mg of 2,2′,3,3′,6′-penta-O-benzyl-4′-O-(deca-O-benzyl -(α-D-matlotriosyl)-4,6-O-benzylidene-α,α-D-trehalose in 10 ml of ethanol and 5 ml of water was hydrogenated at room temperature for 2 hours in the presence of 300 mg of 10% palladium-on-charcoal. The reaction solution was filtered over a filter aid, rinsed and freeze-dried. The crude product was gelchromatographed with water (on Sephadey ® LH20) and the product was lyophilized. There were obtained 65 mg of 4-O-(α-D-maltotriosyl) -α,α-D-trehalose, $[\alpha]_D^{20} = +179.5°$ (c=0.2, $H_2O$).

G. A solution of 30 mg of 4-O-(α-D-maltotriosyl)-α,α-D-trehalose in 1 ml of absolute dimethylformamide was stirred at 50° C. for 20 hours in the presence of 170 mg of sulphur trioxide-trimethylamine complex, whereby a viscous syrup separated. The solvent was decanted off, the residue was washed with methanol, dissolved in 1.5 ml 10% sodium acetate solution and concen- trated. The residue was taken up several times in water and evaporated in order to remove trimethylamine. The residue was gel-chromatographed (Sephadex ® LH 20) in order to remove salts. After freeze-drying there were obtained 67 mg of sulphated 4-O-(α-D-maltotriosyl)-α,α-D-trehalose, S=18.66%, AS (average degree of sulphation) about 24.

The degree of sulphation was estimated from the sulphur content and integration of $^1H$ NMR signals of the quaternary ammonium salt.

EXAMPLE 2

A. A solution of 4.2 g of α-D-acetobromoglucose in absolute dichloromethane was added dropwise at −30° C. to a solution of 3.0 g of dry 2,2′,3,3′,6′-penta-O-benzyl-4,6-O-benzylidene-α,α-D-trehalose in 30 ml of absolute dichloromethane and 2.5 ml of absolute tetramethylurea in the presence of 2.61 g of dry silver trifluoromethanesulphonate. After stirring at room temperature for 20 hours a further addition of 3.44 g of (α-D-acetobromo- glucose in 5 ml of dichloromethane, 2 ml of tetramethylurea and 1.75 g of silver trifluoromethanesulphonate was carried out at −30° C. After stirring at room temperature for 18 hours the mixture was filtered and washed with dichloromethane. The organic solutions were washed with sodium bicarbonate solution and water and dried over magnesium sulphate. Chromatography on silica gel with toluene/ether 6:1 as the eluent gave 64% of pure 4′-O-(2,3,4,6-tetra-O -acetyl-β-D-glucopyranosyl)-2,2′,3,3′,6-penta-O-benzylidene-α,α-D-trehalose as a syrup, $[\alpha]_D^{20} = +53.0°$ (c=0.2, dioxane).

B. A solution of 1.14 g of 4′-O-(2,3,4,6-tetra-O-acetyl-β-D-glucopyranosyl) -2,2′,3,3′,6′-penta-O-benzyl-4,6-O-benzylidene-α,α-D -trehalose in 60 ml of absolute methanol and 20 ml of absolute cyclohexane (20 ml) was treated with 1.4 ml of 2% sodium methylate solution. After 4 hours at room temperature the mixture was neutralized with acidic ion exchanger, filtered, concentrated and chromatographed on silica gel with ethyl acetate/methanol/water 95:1:1 as the eluent, whereby 840 mg of product were obtained. A 370 mg aliquot was hydrogenated at room temperature in 60 ml ethanol/-water 5:1 in the presence of 10% palladium-on-charcoal. After 90 minutes the mixture was filtered, washed with ethanol and water and concentrated. There was obtained a quantitative yield of 4-O-(β-D-glucopyranosyl)-α,α-D-trehalose, $[\alpha]_D^{20} = +121.9°$ (c=0.2, $H_2O$).

C. A solution of 840 mg of well-dried 4-O-(β-D-gluco-pyranosyl) -α,α-D-trehalose in 30 ml absolute dimethyl- formamide was stirred at 50° C. for 20 hours in the presence of 5.08 g of sulphur trioxide-trimethylamine complex, whereby a viscous syrup separated. The solvent was decanted off, the residue was washed with methanol, dissolved in 30 ml of 10% sodium acetate solution and concentrated. The residue was taken up several times in water and evaporated in order to remove trimethylamine. The residue was purified by gel chromatography (Sephadexe ® LH 20) in order to remove salts. After freeze-drying there were obtained 2.0 g of sulphated 4-O-(β-D-glucopyranosyl) -α,α-D-trehalose, S=20.40%, AS about 3.0.

EXAMPLE 3

A. A solution of 1.19 g of hepta-O-acetyl-α-D-maltosyl bromide (J. Chem. Soc. 1962, 2823) in 5 ml of absolute dichloro- methane was added dropwise at 0° C. to a solution of 1.0 g of well-dried 2,2',3,3',6'-penta-O-benzyl-4,6-O-benzylidene-α,α-D-trehalose in 6 ml of absolute dichloromethane and 0.22 ml of tetramethylurea in the presence of 0.43 g of silver trifluoromethanesulphonate. After 8 hours at room temperature 109 mg of silver triflate, 0.05 ml of tetramethylurea and 298 mg of maltosyl bromide were added. After stirring at room temperature for 18 hours the mixture was filtered and washed with dichloromethane. The combined organic solutions were washed with sodium bicarbonate solution and water and dried over magnesium sulphate. Chromatography on silica gel with ethyl acetate/hexane 1:1 as the eluent gave 1.49 g (88%) of pure 4'-O-(hepta-O-acetyl-β-D-maltosyl)-2,2',3,3',6'-penta-O-benzyl-4,6-O-benzylidene-O-α,α-D-trehalose as a syrup, $[\alpha]_D^{20} = +84.0°$ (c=0.2, dioxan).

B. A solution of 1.43 g of 4'-(hepta-O-acetyl-β-D-maltosyl)-2,2', 3,3',6'-penta-O-benzyl-4,6-O-benzylidene-α,α-D-trehalose in 15 ml of absolute methanol and 4 ml of absolute cyclohexane was treated with 6 ml of 2% sodium methylate solution. After 15 minutes at room temperature the mixture was neutralized with acidic ion exchanger, filtered and concentrated. The crude product was dissolved in 20 ml of ethanol/water (3:1) and hydrogenated at room temperature for 2 hours with 275 mg of 10% palladium-on-charcoal. Filtration over a filter aid and rinsing gave pure 4-O-(β-D-maltosyl) -α,α-D-trehalose, (635 mg), $[\alpha]_D^{20} = +150.0°$ (c=0.2, H₂O).

C. A solution of 1.0 g of well-dried 4-O-(β-D-maltosyl)-α,α-D-trehalose in 25 ml of absolute dimethylformamide was stirred at 50° C. for 18 hours in the presence of 5.845 g of sulphur trioxidetrimethylamine complex, whereby a viscous syrup separated. Working-up as described in Example 1G. gave 2.63 g of sulphated 4-O-(β-D-maltosyl)-α,α-D-trehalose, S=19.91%, AS about 2.8.

EXAMPLE 4

A. A solution of 6.67 g of deca-O-acetyl-α-D-maltotriosyl bromide (Carbohydr. Res 48, 197 (1976)) in 40 ml of absolute dichloromethane was added dropwise at −30° C. to a solution of 4.0 g of well-dried 2,2',3,3',6'-penta-O-benzyl-4,6-O-benzylidene-α,α-D-trehalose in 35 ml of absolute dichloromethane and 3.1 ml of tetramethylurea in the presence of 1.74 g of silver trifluoromethanesulphonate. After 3 hours at room temperature 3.4 g of deca-O-acetyl-α-D-maltotriosyl bromide in 20 ml of absolute dichloromethane and 1 g of 4 Å molecular sieves were added at −30° C. The mixture was worked-up after 90 hours. Chromatography on silica gel with ethyl acetate/hexane 3:2 as the eluent gave 4.03 g (50%) of 4'-(deca-O-acetyl -β-D-maltotriosyl)-2,2',3,3',6'-penta-O-benzyl-4,6-O-benzylidene -α,α-D-trehalose as a syrup, $[\alpha]_D^{20} + 100.5°$ (c0.2, dioxane).

B. A solution of 3.46 g of 4'-deca-O-acetyl-β-D-maltotriosyl)-2,2',3,3',6'-penta-O-benzyl-4,6-O-benzylidene-α,α-D-trehalose in 45 ml absolute methanol was stirred at room temperature for 24 hours in the presence of a catalytic amount of anhydrous sodium carbonate. After filtration and neutralization with acidic ion exchanger the mixture was concentrated and chromatographed on silica gel with ethyl acetate/methanol/water 85:10:5 as the eluent. The product fraction (2.29 g, 86%) was dissolved in 24 ml of ethanol/water (5:1) and hydrogenated at room temperature for 3 hours in the presence of 10% palladium-on-charcoal. Filtration over a filter aid and rinsing gave pure 4-O-(β-D-maltotriosyl)-α,α-D-trehalose as a foam (1.21 g, 100%), $[\alpha]_D^{20} = +172.5°$ (c=0.2, H₂O).

C. A solution of 500 mg of well-dried 4-O-(β-D-maltotriosyl)-α,α-D -trehalose in 10 ml of absolute dimethylformamide was stirred at 50° C. for 18 hours in the presence of 2.85 g of sulphur trioxidetrimethylamine complex, whereby a viscous syrup separated. Working-up as described in Example 1G. gave 1.32 g of sulphated 4-O -(β-D-maltotriosyl)-α,α-D-trehalose, S=19.5%, AS about 2.6.

EXAMPLE 5

A. A solution of 1.19 g of dry hepta-O-acetyl-α-D-cellobiosyl bromide (Ann. 435, 1 (1923)) in 5 ml of absolute dichloromethane was added dropwise at −30° C. to a solution of 1 g of well-dried 2,2',3,3',6'-penta-O-benzyl-4,6-O-benzylidene-α,α-D-trehalose in 1 ml of absolute dichloromethane and 0.3 ml tetramethylurea in the presence of 442 mg of silver trifluoromethanesulphonate. After stirring at room temperature for 60 hours the mixture was filtered over a filter aid, rinsed with dichloromethane, evaporated and chromatographed on silica gel with dichloromethane/acetone 24:1 as the eluent. There were obtained 1.51 g (88%) of pure 4'-O-(hepta-O-acetyl -β-D-cellobiosyl)-2,2',3,3',6'-penta-O-benzyl-4,6-O-benzylidene -α,α-D-trehalose, $[\alpha]_D^{20} = +35.0°$ (c=0.3, CHCl₃).

B. A solution of 1.0 of 4'-O-(hepta-O-acetyl-β-D-cello-biosyl)2,240 ,3,3',6'-penta-O-benzyl-4,6-O-benzylidene-(α,α-D-trehalose in 30 ml absolute methanol was stirred at room temperature in the presence of a catalytic amount of sodium (a few mg). After 2 hours the mixture was neutralized with acidic ion exchanger, evaporated and filtered over silica gel in chloroform/methanol 9:1. Evaporation gave a deacetylated crude product (764 mg) of which 168 mg were hydrogenated at room temperature in 10 ml of ethanol/water (4:1) in the presence of 10% palladium-on-charcoal. After 2.5 hours the mixture was filtered over a filter aid, rinsed and evaporated. There were obtained 93 mg (100%) of 4'-O-(β-D-cellobiosyl)-α,α-D-trehalose, $[\alpha]_D^{20} = +97°$ (c=0.3, H₂O).

C. A solution or 72 mg of 4'-O-(β-D-cellobiosyl)-α,α-D-trehalose in 5 ml of anhydrous dimethylformamide was stirred at 5° C. for 20 hours in a presence of sulphur trioxide-trimethylamine complex, whereby a viscous syrup separated. Work-up as described in Example 1G. gave 176 mg of sulphated 4-O-(β-D-cellobiosyl)-α,α-D-trehalose, S=18.2%, AS about 2.7.

EXAMPLE 6

A. 2.19 ml of bistributyltin oxide were added to a suspension of 1.0 g of 2,2',3,3'-tetra-O-benzyl-α,α-D-trehalose (Chem. Pharm. Bull. 30, 1169 (1982)) in 80 ml of toluene and the mixture was heated under reflux in a Dean Stark apparatus for 3.5 hours. Thereby, the volume was reduced by 40 ml. Then, 157 mg of tetrabutylammonium bromide and 0.84 ml of benzyl bromide were added and the mixture was stirred at 80° C. for 30 hours. After the addition of the same amounts of tetrabutylammonium bromide and benzyl bromide the mixture was stirred at 80° C. for a further 72 hours. The reaction mixture was poured into ice-water/methylene chloride and extracted with water and sodium bicarbonate solution. After evaporating the organic phase the residue was chromatographed on silica gel with ethyl acetate/ hexane 1:2 as the eluent. There was obtained pure 2,2'3,3',6'-hexa-O-benzyl-α,α-D-trehalose (1120 mg, 89%) as a syrup, $[\alpha]_D^{20} = +111.5°$ (c=0.5, dioxane).

B. A solution of 2.38 g of hepta-O-acetyl-α-maltosyl bromide in 12 ml of anhydrous dichloromethane was added at −30° C. to a suspension of 1.0 g of 2,2',3,3',6,6'-hexa-O-benzyl-α,α-D-trehalose and 0.88 g of silver triflate in 3 ml of anhydrous dichloromethane and 0.61 ml of tetramethylurea. After 10 days at room temperature the mixture was filtered over a filter aid, washed with dichloromethane, evaporated and the crude product was chromatographed on silica gel with acetone/hexane 2:3 as the eluent. There were obtained 1.96 g of pure 4,4'-bis-O-(hepta-O-acetyl-β-D-maltosyl)-2,2',3,3',6,6'-hexa-O-benzyl-α,α-D-trehalose (82%), melting point 85° C., $[\alpha]_D^{20} = +84.5°$ (c=0.2, chloroform).

C. A catalytic amount of sodium methylate was added at room temperature to a solution of 1.0 g of 4,4'-bis-O-(hepta-O-acetyl-β-D-maltosyl) -2,2',3,3',6,6'-hexa-O-benzyl-α,α-D-trehalose in 40 ml of methanol/-dioxane (1:1). After 4 hours the mixture was neutralized with acidic ion exchanger, filtered and evaporated. The deacetylated compound was dissolved in 50 ml of ethanol/ water (1:1) and hydrogenated at room temperature in the presence of 300 mg of 10% palladium-on-charcoal. After I hour the mixture was filtered over a filter aid, washed with ethanol/ water (1:1) and evaporated. There were obtained 465 mg of pure 4,4'-bis-O-(β-D-maltosyl)-α,α-D-trehalose, $[\alpha]_D^{20} = +148°$ (c=1.3, H₂O).

D. A solution of 0.3 g of 4,4'-bis-O-(β-D-maltosyl)-α,α-D-trehalose in 15 ml of anhydrous dimethylformamide was stirred at 50° C. for 20 hours in the presence of 1.685 g of sulphur trioxide-trimethylamine complex, whereby a viscous syrup separated. Work-up as described in Example 1G. gave 652 mg of sulphated 4,4'-bis-O-(β-D-maltosyi)-α,α-D-trehalose, S=18.93%, AS=2.5.

EXAMPLE 7

A. 0.21 ml of trifluoromethanesulphonic anhydride was added under argon to a cooled solution (−80° C.) of 618 mg of 2,3,4,6-tetra-O-acetyl-D-glucopyranosyl trichloroacetimidate and 553 mg of 2,2',3,3',6,6'-hexa-O-benzyl-α,α-D-trehalose in 5 ml of absolute dichloromethane. After 2.5 hours at −10° C. a further 123 mg of 2,3,4,6-tetra-O-acetyl-D-glucopyranosyl trichloroacetimidate and 41 ml of trifluoromethanesulphonic anhydride were added at −80° C. The mixture was warmed to −10° C., triethylamine was added and the solvent was evaporated. After co-distillation with toluene the residue was chromatographed on silica gel with toluene/ethyl acetate 7:3 as the eluent and there were obtained 832 mg (86%) of pure 4,4'-bis, O-(2,3,4,6-tetra-O-acetyl-β-D-glucopyranosyl)-2,2',3,3',6,6'-hexa-O-benzyl -(α,α-D-trehalose $[\alpha]_D^{20} = +42°$ (c=0.3, chloroform).

B. A solution of 696 mg of 4,4'-bis-O-(2,3,4,6-tetra-O-acetyl-β-D-glucopyranosyl) -2,2',3,3',6,6'-hexa-O-benzyl-α,α-D-trehalose in 40 ml of anhydrous methanol was treated with a catalytic amount of sodium. After 20 minutes at room temperature the mixture was neutralized with acidic ion exchanger, filtered and evaporated. Filtration over silica gel with chloroform/methanol 9:1 as the eluent gave 480 mg of deacetylated compound which was hydrogenated at room temperature in 50 ml of ethanol/water (4:1) in the presence of 200 mg of 10% palladium-on-charcoal. After 2 hours the mixture was filtered over a filter aid, washed with ethanol/water (1:1) and evaporated. There were obtained 250 mg of 4,4'-bis-O-(β-D -glucopyranosyl)-α,α-D-trehalose $[\alpha]_D^{20} = +108°$ (c=0.2, H₂O).

C. A solution of 208 mg of 4,4'-bis-O-(β-D-glucopyranosyl)-α,α-D-trehalose in 5 ml absolute dimethylformamide was stirred at 50° C. for 20 hours in the presence of 1.22 g of sulphur trioxidetrimethylamine complex, whereby a viscous syrup separated. Workup as described as in Example 1G. gave 520 mg of sulphated 4,4'-bis -O-(β-D-glucopyranosyl)-α,α-D-trehalose, S=19.52%, AS about 2.7.

EXAMPLE 8

A. 0.52 g of sliver trifluoromethanesulphonate and immediately thereafter 0.6 ml of absolute tetramethylurea were added at 0°–50° C. to a solution of 2.64 g of high vacuum-dried 2,2',3,3',6'-penta-O-benzyl -4,6-O-benzylidene-α,α-D-trehalose and 1.29 g of 2,3,4-tri-O-acetyl -6-O-(2,3,4-tri-O-acetyl-6-desoxy-α-L-mannopyranosyl)-α-D-glucopyranosyl bromide [Ber. 70, 1098–1101 (1938)] in 20 ml of absolute dichloromethane. After stirring at 0°–50° C. for a further 75 minutes the reaction mixture was suction filtered over Dicalite and rinsed with dichloro- methane, and the filtrate was washed twice with saturated sodium bicarbonate solution, dried over magnesium sulphate and concentrated. The residue was chromatographed on 85 g of silica gel (70–230 mesh) with ethyl acetate/hexane 1:4, 1:2 and 1:1 as the eluent and gave 830 mg (29%) of O-(2,3,4-tri-O-acetyl-6-desoxy-α-L-mannopyranosyl)-(1→46)-O-(2,3,4-tri-O-acetyl-β-D-glucopyranosyl)-(1→4)-2,2',3,3',6'-penta-O-benzyl -4,6-O-benzylidene-(α,α-D-trehalose as a foam, $[\alpha]_D^{20} = +32.2°$ (c=0.5, CHCl₃).

B. 1.5 ml of 1% Na in methanol were added at room temper- ature to a solution of 750 mg of O-(2,3,4-tri-O-acetyl-6-desoxy-α-L-mannopyranosyl) -(1→6)-O-(2,3,4-tri-O-acetyl-β-D-gluco-pyranosyl) -(1→4)-2,2',3,3',6'-penta-O-benzyl-4,6-O-benzylidene-α,α-D-trehalose in 1.5 ml of diethyl ether and 7.5 ml of methanol and the mixture was stiffed for a further 3 hours. The reaction solution was then neutralized with acidic ]on exchanger (Amberlite IR-120), stirred for 30 minutes, filtered off, rinsed with methanol and the filtrate was evaporated. The residue was chromatographed on 27 g of silica gel (70–230 mesh) with ethyl acetate/methanol/water 98:1:1 as the eluent. 380 mg (62%) of deacylated product were obtained, $[\alpha]_D^{20} = +7.0$ (c=0. 1, CHCl₃). 360 mg (0.303 mmol) of this product in 27 ml of ethanol/water 2:1 were hydrogenated at room temperature in the presence of 180 mg of 10% palladium-on charcoal. After 14 hours the reaction mixture was suction filtered over Dicalite, rinsed with ethanol/water and the filtrate was concentrated and dried in a high vacuum. There were obtained 205 mg (100%) of O-(6-desoxy-α-L-mannopyranosyl)-(1→6)-O-β-D-glucopyranosyl-(1→4)-

α,α-D-trehalose as an amorphous powder, $[α]_D^{20} = +9.3°$ (c=0.1, H2O).

C. A solution of 200 mg of O-(6-desoxy-α-L-mannopyranosyl)-(1→6) -O-β-D-glucopyranosyl-(1→4)-α,α-D-trehalose in 7 ml of absolute dimethylformamide was treated with 1.72 g of sulphur trioxide-trimethylamine complex and stirred under argon at 60°-65° C. for 20 hours. A resinous precipitate separated during this time. The solvent was evaporated and the residue was dissolved in 11 ml of 10% sodium acetate solution and concentrated in a water-jet vacuum. The residue was taken up several times (10×) in 50 ml of water each time and evaporated in order to remove, triethylamine and was then gel-chroma- tographed (Sephadex ® LH20, 150 g) in order to remove salts. The fractions containing the sulphated tetrasaccharide were evaporated and lyophilized. There were obtained 320 mg (54%) of sulphated O-(6-desoxy-α-L-mannopyranosyl)-(1→6)-O-β-D-glucopyranosyl) -(1→4)-α,α-D-trehalose as an amorphous powder, S=19.62%, AS=about 2.7.

EXAMPLE 9

A. 0.52 g of silver trifluoromethanesulphonate, 1.40 g of 2,3,4-tri -O-acetyl-6-O-(2,3,4,6-tetrta-O-acetyl-α-D-glucopyranosyl)-α-D-glucopyranosyl bromide [Wolfram et al, J. Am. Chem. Soc., 71, 125–127, (1949)] and 0.6 ml of absolute tetramethylurea (5.0 mmol) were added in rapid sequence at 0°-50° C. to a solution of 2.64 g of high vacuum-dried 2,2',3,3',6'-penta-O-benzyl-4,6-O-benzylidene-α,α-D-trehalose in 20 ml of absoluteichloromethane and the mixture was stirred at 0°-50° C. for a further 1 hour. The reaction mixture was suction filtered over Dicalite, rinsed with dichloromethane, the filtrate was washed twice with saturated sodium bicarbonate solution, dried over magnesium sulphate, filtered off and concentrated. The residue was chromatographed on 85 g of silica gel (70–230 mesh) with ethyl acetate/hexane 1:4, 1:2 and 1:1 as the eluent. 740 mg (25%) of O-(2,3,4,6-tetra-O-acetyl-α-D-glucopyranosyl) -(1→6)-O-(2,3,4-tri-O-acetyl-β-D-glucopyranosyl)-(1 →4)-2,2',3,3',6'-penta-O-benzyl-4,6-O-benzylidene-α,α-D-trehalose were obtained as a foam, $[α]_D^{20} = +78.2°$ (c=0.5, CHCl3).

B. 1.32 ml of I % Na in methanol were added at room temperature to a solution of 660 mg of O-(2,3,4,6-tetra-O-acetyl-α-D -glucopyranosyl)-(1→6)-O-(2,3,4-tri-O-acetyl-β-D-gluco- pyranosyl)(1→4)-2,2',3,3',6'-penta-O-benzyl-4,6-O-benzylideneα,α-D-trehalose in 1.5 ml of diethyl ether and 7.5 ml of methanol and the mixture was stirred at room temperature for a further 3 hours. The reaction solution was then stirred with acidic ion exchanger (Amberlite IR-120) for 10 minutes, filtered off and rinsed with methanol. The filtrate was evaporated and chroma- tographed on 27 g of silica gel (70–230 mesh) with ethyl acetate/methanol/water 96:2:2 as the eluent. 420 mg (79%) of deacylated product were obtained, $[α]_D^{20} = 103.0$ (c=0.1, CHCl3). 400 mg (0.33 mmol) of this product in 30 ml of ethanol/water 2:1 were hydrogenated at room temperature in the presence of 200 mg of 10% palladium-on charcoal. After 14 hours the mixture was suction filtered over Dicalite, rinsed with ethanol/water and the filtrate was concentrated and dried in a high vacuum. There were obtained 230 mg (100%) of O-(α-D-glucopyranosyl)-(→6) -O-(β-D-glucopyranosyl)-(1→4)-α,α-D-trehalose as an amorphous powder, $[α]_D^{20} = +133.0°$ (c=0.1, H2O).

C. A solution of 213 mg of O-(α-D-glucopyranosyl)-(1→6)-O-(β-D-glucopyranosyl) -(1→4)α,α-D-trehalose in 8 ml of dry dimethylformamide was stirred with 1.80 g of sulphur trioxidetrimethylamine complex at 60°-65° C. for 20 hours, whereby a glassy, resinous precipitate separated. After decanting off the solvent the residue was dissolved in 11 ml of 10% sodium acetate solution and concentrated in a water-jet vacuum. The residue was dissolved several times (12×) in 50 ml of water each time and evaporated in order to remove triethylamine. In order to remove salts, the residue was gelchromatographed (Sephadex ® LH20, 150 g). Product fractions were evaporated and lyophilized. There were obtained 390 mg (~58%) of sulphated O-α-D-glucopyranosyl-(1→6)-O-β-D-glucopyranosyl -(1→4)-α,α-D-trehalose as an amorphous powder, S=20.36%, AS=about 3.0.

EXAMPLE 10

A. 1.52 g of silver trifluoromethanesulphonate, 4.13 g of hepta-O-acetyl -α-D-melibiosyl bromide [Jeanes at al, J. Am. Chem. Soc., 75, 3667–3672, (1953)] in 15 ml of absolute dichloromethane and 0.76 ml of absolute tetramethylurea were added successively and rapidly at 0°-50° C. to a solution of 3.84 g of 2,2',3,3',4,6,6'-hepta-O-benzyl -4,6-O-benzylidene-α,α-D-trehalose [S.Kato, K.Yogo, Bull. Chem. Soc. Jpn., 59, 411–14 (1986)] in 25 ml of absolute dichloromethane. After stirring at 0°-50° C. for a further 2 hours the reaction mixture was suction filtered over Dicalite and rinsed with dichloromethane. The filtrate was washed twice with saturated sodium bicarbonate solution, dried over magnesium sulphate, filtered off, concentrated and chromatographed on 350 g of silica gel (70–230 mesh) with ethyl acetate/hexane 1:4, 1:3 and 1:2 as the eluent. 2.93 g (47%) of pure 4-O-(hepta-O-acetyl-β-D-melibiosyl)-2,2',3,3',4,6,6'-hepta-O-benzyl -α,α-D-trehalose were obtained as a foam, $[α]_D^{20} = 93.4°$ (c=0.5, CHCl3).

B. A solution of 2.75 g of 4-O-(hepta-O-acetyl-b-D-melibiosyl) 2,2',3,3',4,6,6'-hepta-O-benzyl-α,α-D-trehalose in,-3.5 ml of diethyl ether and 27 ml of methanol- was treated at room temperature with 5.5 ml of 1% sodium in methanol and stirred for 2½ hours. The reaction solution was then stirred with acidic ion exchanger (Amberlite IR-120) for 10 minutes, filtered off under suction and rinsed with methanol. The filtrate was evaporated and the residue was chromatographed on 75 g of silica gel (70–230 mesh) with ethyl acetate/-methanol/water 96:2:2 as the eluent. 1.53 g (68%) of deacylated product were obtained, $[α]_D^{20} = +115°$ (c=0.2, CHCl3). 1.296 g (10 mmol) of this in 40 ml of ethanol/H2O 3:1 were hydrogenated at room temperature in the presence of 0.7 g of 10% palladium-on-charcoal. After 8 hours the reaction mixture was suction filtered over Dicalite and rinsed with ethanol/water. The filtrate was concentrated and dried in a high vacuum and gave 0.679 g (100%) of 4-O-(β-D-melibiosyl)-α,α-D-trehalose as an amorphous powder, $[α]_D^{20} = +143.2°$ (c=0.5, H2O).

C. A solution of 660 mg of 4-O-(β-D-melibiosyl)-α,α-D-trehalose in 15 ml of dry dimethylformamide was treated with 4.17 g (30 mmol) of sulphur trioxide-trimethylamine complex and stirred at 60°-65° C. for 20 hours, whereby a viscous syrup separated after 3 hours. The solvent was decanted off and the residue was dissolved in 25 ml of 10% sodium acetate solution and concentrated in a water-jet vacuum. The residue was dissolved several times (12×) in 50 ml of water each time and concentrated in order to remove triethylamine. In order to remove salts, the residue was gel-chromatographed (Sephadex ® LH20, 150 g). Fractions containing sulphated tetrasaccharide were evaporated and lyophilized. There were obtained 1.59 g (about 80%) of sulphated 4-O-(β-D -melibiosyl)-α,α-D-trehalose, $[\alpha]_D^{20}= +135.2°$ (c=1.0, H$_2$O), S=20.58%, AS=about 3.0.

EXAMPLE 11

A. 0.37 g of absolute N,N,N,N-tetramethylurea and 0.76 g of dry silver trifluoromethanesulphonate were added at 0°-50° C. under argon and with the exclusion of light to a solution of 1.74 g of dry 2,2',3,3',6'-penta-O-benzyl-4,6-O-benzylidene-α,α-trehalose (Carbohydr. Res. 63, 51, (1978)) in 12.5 ml of absolute dichloromethane. A solution of 1.92 g of acetobromo-D-lactose (J. Am. Chem. Soc. 37, 1270 (1915)) in 7.5 ml of dichloromethane was added dropwise. After stirring at 0°-50° C. for 1.5 hours the reaction solution was filtered over silica gel and washed with dichloromethane. The organic solutions were washed with sodium bicarbonate solution and water and dried over magnesium sulphate. Chromatography on silica gel with ethyl acetate/hexane 1:2 as the eluent gave 1.54 g of pure 4'-O-(hepta-O-acetyl-β-D-lactosyl)-2,2',3,3',6'-penta-O-benzyl-4,6-O-benzylidene -α,α-D-trehalose as a white resin, FAB-MS (1521.2 (M+Na)+).

B. A solution of 1.22 g of 4'-O-(hepta-O-acetyl-β-D-lactosyl) -2,2',3,3',6'-penta-O-benzyl-4,6-O-benzylidene-α,α-D-trehalose in 12.2 ml of absolute methanol and 2.5 ml of absolute ether was treated with 3.1 ml of 1% sodium methylate solution. After 5.5 hours at room temperature the mixture was neutralized with acidic ion exchanger, filtered and concentrated. Chromatography on silica gel with ethyl acetate/methanol/water 85:10:5 as the eluent gave 0.91 g of pure 4'-O-(β-D-lactosyl)-2,2',3,3',6'-penta-O-benzyl -4,6-O-benzylidene-α,α-D-trehalose as a white resin, FAB-MS (1227.3 (M+Na)+).

C. A solution of 0.90 g of 4'-O-(β-D-lactosyl)-2,2',3,3',6'-penta-O -benzyl-4,6-O-benzylidene-α,α-D-trehalose in 28 ml of ethanol/water 3:1 was hydrogenated at room temperature for 6 hours with 0.5 g of 10% palladium-on-charcoal. Filtration over a filter aid and rinsing gave, after drying in a high vacuum, 0.51 g of pure 4'-O-(β-D-lactosyl)-α,α-D-trehalose as a white resin, FAB-MS (689.0 (M+Na)+).

D. A solution of 0.49 g of well-dried 4'-O-(β-D-lactosyl)-α,α-D -trehalose in 11.2 ml of absolute dimethylformamide was stirred at 65° C. for 22 hours in the presence of 3.094 g of sulphur trioxidetrimethylamine complex, whereby a viscous syrup separated. Workup as described in Example 1G gave 1.1 g of sulphated 4'-O-(β-D -lactosyl)-α,α-D-trehalose, S=19.93%, AS about 2.9.

EXAMPLE 12

A. 0.30 g of absolute N,N,N,N-tetramethylurea and 0.625 g of dry silver trifluoromethanesulphonate were added at 0°-5° C. under argon and with the exclusion of light to a solution of 1.43 g of dry 2,2',3,3',6'-penta-O-benzyl-4,6-O-benzylidene-α,α-D-trehalose (Carbohydr. Res. 63, 51, (1978)) in 10.0 ml of absolute dichloromethane. A solution of 1.70 g of acetobromo-D-gentiobiose (J. Am. Chem. Soc. 49, 3170 (1927)) in 6.0 ml of methylene chloride was added dropwise. After stirring at room temperature for 20 hours the reaction solution was filtered over silica gel and washed with dichloromethane. The organic solutions were washed with sodium bicarbonate solution and water and dried over magnesium sulphate. Chromatography on silica gel with ethyl acetate/toluene 1:2 as the eluent gave 1.22 g of pure 4'-O-(hepta-O -acetyl-β-D-gentiobiosyl)-2,2',3,3',6'-penta-O-benzyl-4,6-O -benzylidene-α,α-trehalose as a white resin, FAB-MS (1521.2 (M+Na)+).

B. A solution of 1.22 g of 4'-O-(hepta-O-acetyl-β-D-gentiobiosyl) -2,2',3,3',6'-penta-O-benzyl-4,6-O-benzylidene-α,α-D-trehalose in 12.0 ml of absolute methanol and 2.5 ml of absolute ether was treated with 2.44 ml of 1% sodium methylate solution. After 5.5 hours ar room temperature the mixture was neutralized with acidic ion exchanger, filtered and concentrated. Chromatography on silica gel with ethyl acetate/methanol/water 85:10:5 as the eluent gave 0.50 g of pure 4'-O-(β-D-gentiobiosyl)-2,2',3,3',6'-penta -O-benzyl-4,6-O-benzylidene-α,α-D-trehalose as a white resin, FAB-MS (1227.4 (M+Na)+).

C. A solution of 0.48 g of 4'-O-(β-D-gentiobiosyl)-2,2',3,3',6'-penta -O-benzyl-4,6-O-benzylidene-α,α-D-trehalose in 11 ml of ethanol and 3.7 ml of water 3:1 was hydrogenated at room temperature for 6 hours with 0.27 g of 10% palladium-on-charcoal. Filtration over a filter aid and rinsing gave, after drying in a high vacuum, 0.26 g of pure 4'-O-(β-D-gentiobiosyl)α,α-D-trehalose, as a white resin, FAB-MS (689.0 ((M+Na)+).

D. A solution of 0.20 g of well-dried 4'-O-(β-D-gentiobiosyl)-α,α-D-trehalose in 5.0 ml of absolute dimethylformamide was stirred at 65° C. for 22 hours in the presence of 1.26 g of sulphur trioxidetrimethylamine complex, whereby a viscous syrup separated. Working-up as described in Example 1G gave 0.50 g of sulphated 4'-O -(β-D-gentiobiosyl)-α,α-D-trehalose, S=20.25%, AS about 3.3.

EXAMPLE 13

A. 50 ml of acetic anhydride were added to a suspension of 5 g of 3-O-β-D-galactopyranosyl-D-arabinose in 75 ml of pyridine and the mixture was stirred at room temperature for 6 hours. The reaction solution was concentrated in a water-jet vacuum at <40° C. bath temperature. The syrupy residue was treated with 200 ml of ice-water and extracted twice with 200 ml of ethyl acetate each time. The extracts were washed twice with cold 5% H$_2$SO$_4$, twice with saturated sodium bicarbonate solution and once with saturated sodium chloride solution, dried over magnesium sulphate, filtered off and evaporated and dried in a high vacuum overnight. There were obtained 8.84 g (91 %) of 1,2,4-tri-O-acetyl-3-O-(2,3,4,6-tetra-O -acetyl-β-D-galactopyranosyl)-D-arabinose (according to NMR the mixture also contained furanose derivative). 7.6 g thereof were dissolved in 15 ml of dichloromethane, cooled to 0° C. and treated within 15' with 45 ml of 33% hydrobromic acid in acetic acid and stirred at 0° C. for a further 2 hours. The reaction mixture was poured on to 250 ml of ice-water and extracted three times with 100 ml of dichloromethane each time. The extracts were washed twice with 100 ml of ice-water each time and twice with 100 ml of cold saturated sodium bicarbonate solution each time, dried over magnesium sulphate, filtered off and evaporated at <25° C. The residue was chromatographed on 200 g of silica gel (70–230 mesh) with dichloromethane/diethyl ether 9:1 and 4:1 as the eluent. There were obtained 4.15 g (53%) of 2,4-di-O-acetyl-3-O-(2,3,4,6-tetra-O-acetyl-β-D-galacto-pyranosyl)-β-D-arabinopyranosyl bromide in the form of a foam, $[\alpha]_D^{20} = -148.8°$ (c=0.5, CHCl₃).

B. 2.0 ml of absolute tetramethylurea and 1.55 g of silver trifluoromethanesulphonate were added in succession at 0°-5° C. to a solution of 3.52 g of high vacuum-dried 2,2',3,3',6'-penta-O-benzyl-4,6-O-benzylidene-α,α-D-trehalose and 3.76 g of 2,4-di-O-acetyl-3-O-(2,3,4,6-tetra-O-acetyl-β-D-galactopyranosyl)-β-D-arabinopyranosyl bromide in 30 ml of absolute dichloromethane. After one hour at 0°-5° C. the reaction mixture was suction filtered over Celite, rinsed with dichloromethane, the filtrate was washed twice with saturated sodium bicarbonate solution, dried over magnesium sulphate, filtered off and evaporated. The residue was chromatographed on 190 g of silica gel (70–230 mesh) with ethyl acetate/hexane 1:2 and 1:1 as the eluent. There were obtained 3.33 g (58%) of O-(2,3,4,6-tetra-O-acetyl-β-D-galactopyranosyl) -(1→3)-O-(2,4-di-O-acetyl-α-D-arabinopyranosyl)-(1→4)-2,2',3,3',6'-penta-O-benzyl-4,6-O-benzylideneα,α-D-trehalose as a foam, $[\alpha]_D^{20} 42.0°$ (c=0.5, CHCl₃).

C. 3.4 ml of 1% Na in methanol were added to a solution of 3.4 g of O-(2,3,4,6-tetra-O-acetyl-β-D-galactopyranosyl)-(1→3)-O-(2,4-di -O-acetyl-α-D-arabinopyranosyl)-(1→4)-2,2',3,3',6'-penta-O-benzyl-4,6-O-benzylidene-α,α-D-trehalose in 7 ml of diethyl ether and 35 ml of methanol and the mixture was stirred at room temperature for 1.5 hours. The reaction solution was neutralized with ion exchanger (Amberlite IR-120), stirred for 15 minutes, filtered off, rinsed with methanol and the filtrate was evaporated. The residue was chromatographed on 90 g of silica gel (70–230 mesh) with ethyl acetate/methanol/ water 93:5:2 as the eluent. 1.93 g (69%) of deacylated product were obtained as a foam, $[\alpha]_D^{20} = +52.0$ (c=0.5, CHCl₃). 1.80 g (1.53 mmol) of this in 60 ml of ethanol/water 3:1 were hydrogenated at room temperature in the presence of 1.0 g of 10% palladium-on charcoal. After 16 hours the reaction mixture was suction filtered over Dicalite, rinsed with ethanol/water and the filtrate was evaporated and dried. There were obtained 1.12 g of a product which, for further purification, was acetylated using pyridine (22 ml) and acetic anhydride (11 ml). After 22 hours at room temperature the reaction mixture was evaporated and chromatographed on 85 g of silica gel (70–230 mesh) with ethyl acetate/hexane 1:1 and 2:1 as the eluent. There were obtained 1.06 g (59%) of O-(2,3,4,6-tetra-O-acetyl-β-D-galactopyranosyl) -(1→3)-O-(2,4-di-O-acetyl-α-D-arabinopyranosyl)-(1→4)-hepta-O -acetyl-α,α-trehalose as a foam, $[\alpha]_D^{20} = +68.0°$ (c=0.4, CHCl₃). 1.02 g (0.86 mmol) of this were dissolved in 30 ml of methanol/dimethoxyethane/water 1:1:1 and treated dropwise with 1% sodium methylate solution (pH 12-13) until saponification was complete. After 6 hours the reaction solution was neutralized with ion exchanger (Amberlite IR-120), stirred for 15 minutes, suction filtered, rinsed with methanol/water and the filtrate was evaporated and dried in a high vacuum. There were obtained 480 mg (88%) of O-β-D-galactopyranosyl-(1→3)-O-α-D-arabino- pyranosyl-(1→4)-α-α-trehalose as an amorphous powder, $[\alpha]_D^{20} = +9.4°$ (c=0. 1, H₂O).

D. A solution of 440 mg (0.69 mmol) of O-β-D-galactopyranosyl-(1→3)-O-α-D-arabinopyranosyl-(1→4)-α,α-trehalose in 15 ml of dry dimethylformamide was treated with 2.87 g (20.7 mmol) of sulphur trioxide-trimethylamine complex and stirred at 60°-65° C. under argon for 20 hours. During this time a viscous precipitate separated. Working-up as described in Example 1G gave 960 mg (about 75%) of sulphated O-β-D-galactopyranosyl-(1→3)-O -α-D-arabinopyranosyl-(1→4)-α,α-trehalose as an amorphous powder, $[\alpha]_D^{20} = +158.8°$ (c=0.5, H₂O), S=19.24%, AS about 3.0.

EXAMPLE 14

For the production of an injection solution, 5 mg of a compound of formula I and 9 mg of sodium chloride are dissolved in water ad 1 ml. The solution is treated with ascorbic acid (0.5 mg/ml) and benzyl alcohol (0.1 mg/ml) and then filtered sterile.

we claim:

1. Oligosaccharides of the formula

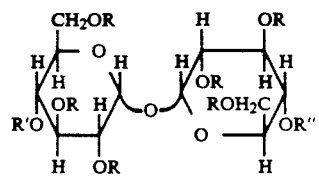

wherein R is hydrogen or the sulfate residue —SO₃M; M is a cation; R' is an equatorially or quasiequatorially linked mono- , di- or trisaccharide; and R" is hydrogen or an equatorially or quasiequatorially linked mono- or disaccharide; with said mono-, di- or tri-saccharides which form R' and R": being sulfated with said sulfate residue; said oligosaccharide containing a maximum of 6 monosaccharide units and an average of at least one —SO₃M per monosaccharide unit.

2. The oligosaccharide of claim 1 wherein R' is an equatorially linked mono-, di- or trisaccharide and R" is hydrogen or an equatorially linked mono- or disaccharide.

3. The oligosaccharide of claim 1 wherein each said saccharide contains 6-membered rings.

4. The oligosaccharide of claim 3 wherein R' is sulfated β-glucosyl, β-maltosyl, β-cellobiosyl or β-maltotriosyl.

5. The oligosaccharide of claim 3 wherein said oligosaccharide contains 3 monosaccharide units.

6. The oligosaccharide of claim 3 wherein said oligosaccharide is sulphated 4-O-(β-D-glucopyranosyl)α,α-D-trehalose.

7. The oligosaccharide of claim 3 wherein said oligosaccharide contains 4 monosaccharide units.

8. The oligosaccharide of claim 7 wherein R" is hydrogen.

9. The oligosaccharide of claim 8 wherein said oligosaccharide is sulphated 4-O-(β-D-maltosyl)α,α-D-trehalose.

10. The oligosaccharide of claim 8 wherein said oligosaccharide is sulphated 4-O-(β-D-cellobiosyl)-α,α-D-trehalose.

11. The oligosaccharide of claim 8 wherein said oligosaccharide is sulphated 4-O-(β-D-melibiosyl)-α,α-D-trehalose.

12. The oligosaccharide of claim 8 wherein said oligosaccharide is sulphated 4'-O-((β-D-lactosyl)-α,α-D-trehalose.

13. The oligosaccharide of claim 8 wherein said oligosaccharide is sulphated 4'-O-((β-D-gentiobiosyl)-α,α-D-trehalose.

14. The oligosaccharide of claim 7 wherein R" is a saccharide.

15. The oligosaccharide of claim 14 wherein said oligosaccharide is sulphated 4,4'-bis-O-(β-D-glucopyranosyl)-α,α-D-trehalose.

16. The oligosaccharide of claim 14 wherein said oligosaccharide is sulphated O-(6-desoxy-α-L-mannopyranosyl) -(1→6)-O-β-D-glucopyranosyl)-(1→4)-α,α-D-trehalose.

17. The oligosaccharide of claim 14 wherein said oligosaccharide is sulphated O-α-D-glucopyranosyl-(1→6)-O-β-D -glucopyranosyl-(1→4)-α,α-D-trehalose.

18. The oligosaccharide of claim 14 wherein said oligosaccharide is sulphated O-β-D-galactopyranosyl-(1→3)-O-α-D -arabinopyranosyl-(1→4)-α,α-trehalose.

19. The oligosaccharide of claim 3 wherein said oligosaccharide contains 5 monosaccharide units.

20. The oligosaccharide of claim 19 wherein said oligosaccharide is sulphated 4-O-(β-D-maltotriosyl)-α,α-D-trehalose.

21. The oligosaccharide of claim 3 wherein said oligosaccharide contains 6 monosaccharide units.

22. The oligosaccharide of claim 21 wherein said oligosaccharide is sulphated 4,4'-bis-O-(β-D-maltosyl-)α,α-D-trehalose.

* * * * *